United States Patent [19]

Adams et al.

[11] Patent Number: 5,281,361
[45] Date of Patent: Jan. 25, 1994

[54] BLEACHING COMPOSITION

[75] Inventors: Christopher J. Adams, Oxton, Great Britain; Stephen A. Madison, Valley Cottage, N.Y.; John Oakes, Winsford; David W. Thornthwaite, Neston, both of Great Britain

[73] Assignee: Lever Brothers Company, Division of Conopco, Inc., New York, N.Y.

[21] Appl. No.: 706,818

[22] Filed: May 29, 1991

[30] Foreign Application Priority Data

May 30, 1990 [GB] United Kingdom ............... 9012001

[51] Int. Cl.$^5$ ..................... C09K 3/00; C07C 255/00
[52] U.S. Cl. ..................... 252/786.38; 252/186.39; 558/452; 558/455
[58] Field of Search ............ 252/186.38, 186.39; 558/452, 455

[56] References Cited

U.S. PATENT DOCUMENTS

| | | | |
|---|---|---|---|
| 3,882,035 | 5/1975 | Loffelman et al. | 252/186.38 X |
| 4,066,771 | 1/1978 | Strycker | 424/267 |
| 4,120,809 | 10/1978 | Murray | 252/102 X |
| 4,199,466 | 4/1980 | Benson, Jr. | 252/95 X |
| 4,420,614 | 12/1983 | Wilshire et al. | 544/163 |
| 4,915,863 | 4/1990 | Aoyagi et al. | 252/102 |
| 4,978,770 | 12/1990 | Aoyagi et al. | 558/455 |

FOREIGN PATENT DOCUMENTS 2131296  9/1987  Japan.
2084499  9/1988  Japan.
1090296 11/1988  Japan.

*Primary Examiner*—Richard D. Lovering
*Assistant Examiner*—Joseph D. Anthony
*Attorney, Agent, or Firm*—Milton L. Honig

[57] ABSTRACT

Novel cationic nitriles, methods of preparing such nitriles and use thereof as cationic peroxyacid bleach precursor in bleaching (detergent) compositions are disclosed.

The novel cationic nitriles are non-hygroscopic and are characterized in that they have a counter-anion $X^-$ selected from the group consisting of 1) $R\text{-}SO_3^-$, 2) $R\text{-}SO_4^-$, 3) $R\text{-}CO_2^-$, wherein R is a straight or branched chain, optionally substituted, alkyl, alkylether or alkylene group containing 4 to 20 carbon atoms, or a phenyl or alkyl phenyl group containing 6 to 20 carbon atoms, and 4) any other surfactant anion not falling under the groups 1), 2) and 3).

11 Claims, No Drawings

BLEACHING COMPOSITION

BACKGROUND OF THE INVENTION

1. Field of the Invention

This invention relates to cationic nitriles and to an improved bleach composition and a bleaching detergent composition containing said cationic nitrile to serve as a peroxyacid bleach precursor.

2. The Related Art

It is known that the bleach activity of hydrogen peroxide bleach compounds, such as the perborates, percarbonates, persilicates and perphosphates, can be improved so as to become effective at lower wash temperatures, i.e. at or below 60° C., by the use of peroxyacid bleach precursors, often also referred to as bleach activators.

Numerous substances have been disclosed and proposed in the art as usable peroxyacid bleach precursors. Conventionally, these precursors are reactive organic compounds having an O-acyl or N-acyl group, such as carboxylic acid esters, that in alkaline solutions containing a source of hydrogen peroxide will generate the corresponding peroxyacids, a reaction which is also referred to as perhydrolysis. They can be represented by the following general formula:

wherein R can be any suitable radical forming the RCO (acyl) radical and L is a suitable leaving group. It is believed that the reaction with hydrogen peroxide proceeds as follows:

$$RCO—L + OOH^- \rightarrow RCO—OOH + L^-$$

A leaving group is thus any group that is displaced from the peroxyacid bleach precursor as a consequence of nucleophilic attack on the precursor by the hydroperoxide anion. This, i.e. the perhydrolysis reaction, results in the formation of the peroxyacid. Generally, for a group to be a suitable leaving group, it must exert an electron-attracting effect, which facilitates expulsion of the leaving group from the tetrahydral intermediate formed by nucleophilic attack by the hydroperoxide anion. Many and diverse leaving group structures have been described in the patent literature (see, for example, EP-A-0120591). Not only do leaving groups add extra weight to bleach precursors of the conventional type but, once expelled from the precursor as a consequence of nucleophilic attack, they will remain as substantially useless by-products in the bleach solution.

Examples of the most representative precursors of this broad class include N,N,N',N'-tetraacetyl ethylene diamine (TAED), glucose pentaacetate (GPA), xylose tetraacetate (TAX), sodium-4-benzoyloxy benzene sulphonate (SBOBS), sodiumtrimethyl hexanoyloxy benzene sulphonate (STHOBS), tetraacetyl glucoluril (TAGU), tetraacetyl cyanuric acid (TACA), di-N-acetyldimethyl glyoxine (ADMG) and I-phenyl-3-acetylhydantoin (PAH)—see, for example, GB-A-836,988; GB-A-907,356; EP-A-0098129 and EP-A-0120591, which represent only a small part of the large amount of patent literature disclosing precursors.

Recently, cationic peroxyacid precursors have attracted interest of Research workers as substantive and highly effective bleach activators. The same above-indicated general formula also applies to the general class of cationic peroxyacid precursors, but with the special feature of R being a radical containing a quaternary ammonium or quaternary phosphonium group, i.e.

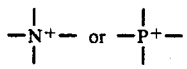

Such cationic peroxyacid precursors are described in, for example, GB-A-1,382,594; U.S. Pat. No. 4,751,015; EP-A-0284292 and EP-A-0331229.

Cationic nitriles form a special class of cationic peroxyacid precursors. These compounds are described in EP-A-0303520 and are said to have at least one of the following groups (a) and (b):

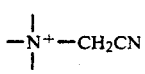

(a)

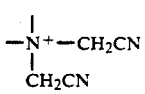

(b)

It is suggested here that the presence of the cationic group $\equiv N^+—CH_2CN$ is essential for the compound to exert its function as effective peroxyacid precursor.

An advantage of these compounds is that they do not contain a leaving group as has routinely been the convention. It is believed that, upon perhydrolysis, they generate a peroxyimidic acid as the highly reactive bleaching species, without the loss of weight involved in having an attached leaving group, as diagrammatically illustrated in the following reaction:

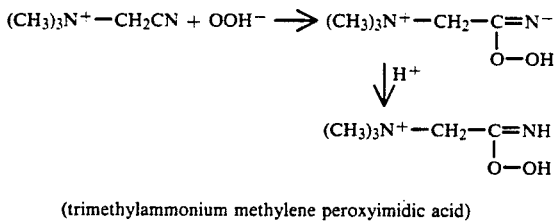

(trimethylammonium methylene peroxyimidic acid)

A serious drawback of the cationic nitriles of the art, however, is their highly hygroscopic nature. It has been observed that the cationic nitriles of the art, e.g. $(CH_3)_3N^+—CH_2CN\ Cl^-$, take up water fairly quickly and deliquesce already upon exposure to an atmosphere of relative humidity of less than about 30% at ambient temperatures. Eventually they will hydrolyze and form the corresponding inactive amide, e.g.

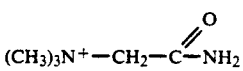

It is therefore an object of the invention to provide an improved and effective cationic peroxyacid precursor without a leaving group, wherein the above drawback is mitigated or even removed, thereby enabling its commercial exploitation.

Having a cationic group, cationic nitriles, just like any other cationic compound, require in their existence the presence of a counter-anion $X^-$, such as $Cl^-$, $I^-$, $NO_3^-$ and the like, $Cl^-$ being the most common anion.

SUMMARY OF THE INVENTION

It has no surprisingly been discovered that the type and size of the counter-ion $X^-$ play an important role in controlling the hygroscopic properties of cationic nitriles.

The above and other objects, which will be apparent in the further description, can be achieved according to the invention by providing a cationic nitrile with a counter-anion selected from the group consisting of:
1) $R-SO_4^-$,
2) $R-SO_3^-$,
3) $R-CO_2^-$, wherein R is a straight or branched chain, optionally substituted alkyl, alkylether or alkylene group containing 4 to 20 carbon atoms, preferably 6 to 18 carbon atoms; or a phenyl or alkylphenyl group containing 6 to 20 carbon atoms, preferably from 7 to 18 carbon atoms, and 4) any other surfactant anions not falling under the groups 1), 2) and 3). By surfactant anion is meant here the anionic surfactant moiety without a salt- or acid-forming cation, such as an alkylbenzene sulphonate-, a sulpho-fatty acid- and a sulphosuccinate-anion.

The cationic nitriles usable herein as peroxyacid bleach precursor with the above-defined counter anion are compounds having at least one of the following cationic groups (A) and (B)

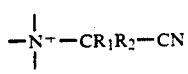

(A)

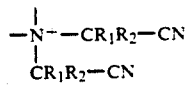

(B)

wherein $R_1$ and $R_2$ are each individually H, or a substituent group containing at least one carbon atom. Suitable substituent groups are, for example, straight or branched chain $C_1-C_8$ alkyl, alkenyl and alkylether groups; phenyl, $C_1-C_3$ alkylphenyl and pyridyl groups, preferably methyl and phenyl groups.

The improved cationic nitriles of the invention are thus compounds of the general formula:

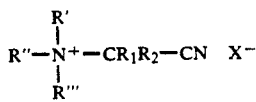

wherein $R_1$ and $R_2$ are as defined above; R' can be any suitable substituent including a straight or branched chain $C_1-C_{24}$ alkyl, alkenyl or alkylether group, or $-CR_1R_2CN$; R" and R''' are each individually a $C_1-C_4$ alkyl or hydroxyalkyl group; or R" can also be

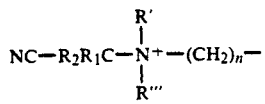

wherein n is an integer from 1 to about 4, forming compounds with two cationic functional groups connected via an alkylene bridging group; and $X^-$ is $R-SO_3^-$, $R-SO_4^-$, $R-CO_2^-$, wherein R is as defined hereinbefore, or any other surfactant anion.

Preferably, R' is $C_1-C_4$ alkyl or a $-CR_1R_2CN$ group, and R" and R''' are each $C_1-C_4$ alkyl; with particular preference to R', R" and R''' being methyl, thus forming cationic nitriles having a trimethyl ammonium group.

Accordingly, in one aspect the invention provides an improved novel cationic peroxyacid precursor in the form of a cationic nitrile having a counter-anion selected from $R-SO_3^-$, $R-SO_4^-$, $R-CO_2^-$ and surfactant anions, as defined hereinbefore.

Examples of suitable counter-anions are alkane and paraffin sulphonates; p-toluene sulphonate; dodecyl benzene sulphonate; $C_{12}-C_{18}$ primary alcohol sulphates, such as lauryl sulphate; lauryl ether sulphate; and $C_8-C_{17}$ alkyl carboxylic acid anions.

A means for characterizing the hygroscopicity of cationic nitriles is by measuring the equilibrium-relative humidity; this is the RH of the headspace at which the sample commences to take up water and deliquiesce at a temperature of 28° C.

Whereas cationic nitriles with conventional counter-anions, such as chloride, bromide, iodide, nitrate, sulphate and methylsulphate, show equilibrium-relative humidity (RH) of only up to about 40%, it is surprising that with the counter-anions of the present invention the equilibrium RH of the cationic nitrile peroxyacid precursors can be increased to a substantial degree.

Preferred counter-anions within the above-defined classes are those which bring the equilibrium RH of the cationic nitrile to a value of at least 60%, preferably at least 70%.

Particularly preferred counter-anions are surfactant anions and $R-SO_3^-$ wherein R is an alkylphenyl group, such as a tosylate anion, i.e. p-toluene sulphonate ion.

In another aspect, the invention provides a bleaching (detergent) composition comprising a peroxide compound bleach and a cationic peroxyacid bleach precursor, wherein said precursor is a cationic nitrile having a counter-anion selected from $R-SO_3^-$, $R-SO_4^-$, $R-CO_2^-$ and surfactant, anions as defined hereinbefore.

DETAILED DESCRIPTION

The cationic nitrile peroxyacid precursor of the invention can be utilized with hydrogen peroxide or a hydrogen peroxide source in the form of solid peroxide compound, such as sodium perborate and sodium percarbonate, in molar ratios of hydrogen peroxide to cationic nitrile precursor of at least 1:1, at pH of at least 7.5 and already at a temperature of as low as 10° C.

Advantageously, the cationic nitrile bleach precursor of the invention is used in the bleaching composition of the invention at molar ratios of peroxide to nitrile from about 2:1 to 20:1, preferably from 5:1 to 12:1, said bleaching composition having a 1-5 g/l solution pH of between 8 and 12, preferably from 8.5 to 10.5, and at a temperature of from about 20° C. to about 60° C., preferably from 30° C. to 50° C.

Examination of the mechanism of the reaction between hydrogen peroxide and cationic nitriles has shown that, when cationic nitriles are added to alkaline solutions containing a source of hydrogen peroxide, various reactions are taking place which compete with each other, the rates of which will be dependent on the reaction conditions.

Without wishing to be bound to any theory, it is believed that the formation of peroxyimidic acid, which is the active bleaching species, occurs almost instantaneously within a few seconds, followed by a relatively slower decay to the corresponding amide:

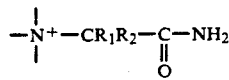

via hydrolysis or by mutual decomposition with hydrogen peroxide.

Optimum bleaching performance is achieved at peroxide to nitrile molar ratio of $\geq 5:1$, at pH $\geq 9$ and at a temperature of about 40° C.

Decrease of peroxide bleach level (i.e. at lower peroxide/nitrile molar ratios) enhances hydrolytic instability, which is suppressed by increasing the peroxide level (i.e. increasing ratio peroxide to nitrile). Below pH 9, yields of peroxyimidic acid decrease, owing to insufficient perhydrolysis and the maximum in bleach performance at 40° C. results from (excessive) increase of bleach instability at temperatures of above 40° C.

The novel cationic nitrile of the invention can be prepared according to the following synthesis routes, diagrammatically written by way of illustration:

By Direct Synthesis:

(1)

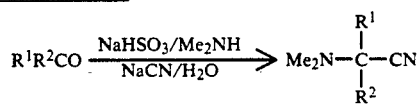

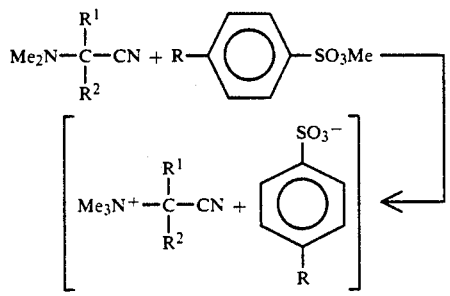

(2)

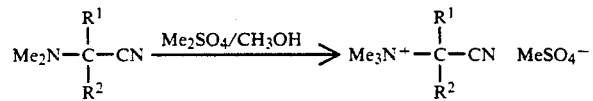

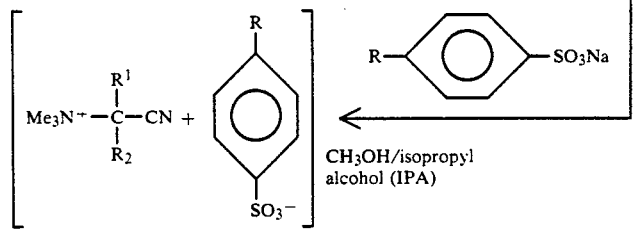

(3) By Solvent Ion-Exchange

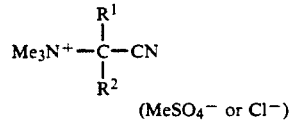

(MeSO$_4^-$ or Cl$^-$)

CH$_3$OH
IPA

+ (i) C$_{15}$H$_{31}$CO$_2$Na
or
(ii) C$_{18}$H$_{37}$OSO$_3$Na
or
(iii) Na-toluene sulphonate (NaOTS)

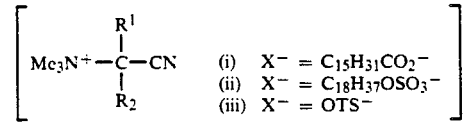

+ NaCl or NaMeSO$_4$ wherein $R^1$ is alkyl or H; and $R^2$ and R are alkyl groups.

An alternative to the ion-exchange route is by intimately dry-mixing the sodium salt of $RSO_3^-$, $RSO_4^-$, $RCO_2^-$ or surfactant with a cationic nitrile with common anion at molar ratios of from 0.5:1 to 10:1. Generally, mixtures thus prepared are of an amorphous nature different from the crystalline salts obtained by solvent ion-exchange, though mixtures as obtained from 1:1 mixtures with primary alcohol sulphate or tosylate salts still have equilibrium RH>70%. Mixtures thus obtained and use thereof are therefore also within the purview of the present invention.

When the invention is applied to bleaching detergent compositions, the formulation, in addition to the essential peroxide compound and cationic nitrile bleach precursor, will usually contain a surface-active material, and desirably also detergency builders and other known ingredients commonly used in detergent compositions.

Peroxide bleach compounds usable in the present invention include the alkali metal peroxides, organic peroxides such as urea peroxide, and inorganic persalts, such as the alkali metal perborates, percarbonates, perphosphates, persilicates and persulphates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous solutions. Sodium percarbonate may be preferred for environmental reasons.

Alkylhydroperoxides are another suitable class of peroxygen compounds. Examples of these materials include cumene hydroperoxide and t-butyl hydroperoxide.

In such formulations the novel cationic nitrile peroxyacid precursor of the invention may be present at a level ranging from about 0.1% to 20% by weight, preferably from 0.5% to 10% by weight, particularly from 1% to 7.5% by weight, together with a peroxide bleaching compound, e.g. sodium perborate tetra- or monohydrate and sodium percarbonate, the amount of which is usually within the range of from about 2% to 40%, preferably from about 4% to 30%, particularly from about 10% to 25% by weight.

The surface-active material may be naturally derived, such as soap, or a synthetic material selected from anionic, nonionic, amphoteric, zwitterionic, cationic actives and mixtures thereof. Many suitable actives are commercially available and are fully described in literature, for example in "Surface Active Agents and Detergents", Volumes I and II, by Schwartz, Perry and Berch. The total level of the surface-active material may range up to 50% by weight, preferably being from about 1% to 40% by weight of the composition, most preferably 4 to 25%.

Synthetic anionic surface-actives are usually water-soluble alkali metal salts of organic sulphates and sulphonates having alkyl radicals containing from about 8 to about 22 carbon atoms, the term alkyl being used to include the alkyl portion of higher aryl radicals.

Examples of suitable synthetic anionic detergent compounds are sodium and ammonium alkyl sulphates, especially those obtained by sulphating higher ($C_8$–$C_{18}$) alcohols produced, for example, from tallow or coconut oil; sodium and ammonium alkyl ($C_9$–$C_{20}$) benzene sulphonates, particularly sodium linear secondary alkyl ($C_{10}$–$C_{15}$) benzene sulphonates; sodium alkyl glyceryl ether sulphates, especially those esters of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $Cl_2$ and then hydrolyzing with a base to produce a random sulphonate; sodium and ammonium $C_7$–$C_{12}$ dialkyl sulphosuccinates; and olefin sulphonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with the anionic surface-active compounds, include in particular the reaction products of alkylene oxides, usually ethylene oxide, with alkyl ($C_6$–$C_{22}$) phenols, generally 5-25 EO, i.e. 5-25 units of ethylene oxides per molecule; the condensation products of aliphatic ($C_8$–$C_{18}$) primary or secondary linear or branched alcohols with ethylene oxide, generally 6-30 EO, and products made by condensation of ethylene oxide with the reaction products of propylene oxide and ethylene diamine. Other so-called nonionic surface-actives include alkyl polyglycosides, long chain tertiary amine oxides, long chain tertiary phosphine oxides and dialkyl sulphoxides.

Amounts of amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

As stated above, soaps may also be incorporated in the compositions of the invention, preferably at a level of less than 25% by weight. They are particularly useful at low levels in binary (soap/anionic) or ternary mixtures together with nonionic or mixed synthetic anionic and nonionic compounds. Soaps which are used are preferably the sodium, or, less desirably, potassium salts of saturated or unsaturated $C_{10}$–$C_{24}$ fatty acids or mixtures thereof. The amount of such soaps can be varied between about 0.5% and about 25% by weight, with lower amounts of about 0.5% to about 5% being generally sufficient for lather control. Amounts of soap between about 2% and about 20%, especially between about 5% and about 10%, are used to give a beneficial effect on detergency. This is particularly valuable in compositions used in hard water when the soap acts as a supplementary builder.

The detergent compositions of the invention will normally also contain a detergency builder. Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the akali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. Nos. 4,144,226 and 4,146,495.

Examples of precipitating builder materials include sodium orthophosphate, sodium carbonate and long chain fatty acid soaps.

Examples of calcium ion-exchange builder materials include the various types of water-insoluble crystalline or amorphous aluminosilicates, of which zeolites are the best known representatives.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethyl malonate, carboxymethyloxy succinate and the water-insoluble crystalline or amorphous aluminosilicate builder materials, or mixtures thereof.

These builder materials may be present at a level of, for example, from 5 to 80% by weight, preferably from 10 to 60% by weight.

Apart from the components already mentioned, the detergent compositions of the invention can contain any of the conventional additives in the amounts in which such materials are normally employed in fabric washing detergent compositions. Examples of these additives include lather boosters, such as alkanolamides, particularly the monoethanol amides derived from palmkernel fatty acids and coconut fatty acids, lather depressants, such as alkyl phosphates and silicones, anti-redeposition agents, such as sodium carboxymethyl cellulose and alkyl or substituted alkyl cellulose ethers, other stabilizers, such as ethylene diamine tetraacetic acid, fabric softening agents, inorganic salts, such as sodium sulphate, and, usually present in very small amounts, fluorescent agents, perfumes, enzymes, such as proteases, cellulases, lipases and amylases, germicides and colourants. The peroxyacid bleach precursors described herein are useful in a variety of cleaning products. These include laundry detergents, laundry bleaches, hard surface cleaners, toilet bowl cleaners, automatic dishwashing compositions and also denture cleaners. Precursors of the present invention can be introduced in a variety of product forms including powders, on sheets or other substrates, in pouches, in tablets or in non-aqueous liquids, such as liquid nonionic detergents.

Generally, for reasons of stability and handling, the bleach precursors will advantageously be presented in the form of particulate bodies comprising said bleach precursor and a binder or agglomerating agent. Many and diverse methods of preparing such precursor particulates have been described in various patent literature documents, such as e.g. in Canadian Patent No. 1,102,966; GB Patent No. 1,561,333; U.S. Pat. No. 4,087,369; EP-A-0,240,057; EP-A-0,241,962; EP-A-0,101,634 and EP-A-0,062,523. Each of these methods may be selected and applied to the bleach precursor of the invention.

Particulates incorporating the precursors of the present invention are normally added to the detergent base composition with the other dry-mix ingredients, such as enzymes, inorganic peroxygen bleaches and suds depressants. It will be appreciated, however, that the detergent composition to which the precursor particulates are added may itself be made in a variety of ways, such as spray-drying, part-part processing, non-tower route processing, dry-mixing, agglomeration extrusion, flaking etc., such ways being well known to those skilled in the art and not forming the essence of the present invention.

The peroxyacid precursors of the present invention can also be incorporated in detergent additive products. Such additive products are intended to supplement or boost the performance of conventional detergent compositions and may contain any of the components of such compositions, although they will not comprise all of the components present in a fully formulated detergent composition. Additive products in accordance with this aspect of the invention will normally be added to an aqueous liquor containing a source of (alkaline) hydrogen peroxide, although in certain circumstances a source of alkaline hydrogen peroxide may be included in the product.

Additive products in accordance with this aspect of the invention may comprise the compound alone in combination with a carrier, such as a compatible particulate substrate, a flexible non-particulate substrate or a container (e.g. pouch or sachet).

Examples of compatible particulate substrates include inert materials, such as clays and other aluminosilicates including zeolites both natural and synthetic of origin. Other compatible particulate carrier materials include hydratable inorganic salts, such as phosphates, carbonates and sulphates.

Additive products enclosed in bags or containers can be manufactured such that the containers prevent egress of their contents when dry but are adapted to release their contents on immersion in an aqueous solution.

In a further specific embodiment, the peroxyacid precursors of the invention are particularly suitable for incorporation in so-called non-aqueous liquid laundry detergent compositions together with a peroxide bleaching compound, e.g. sodium perborate, to impart an effective cleaning and stain-removing capacity to the products on fabrics and textiles.

Non-aqueous liquid detergent compositions including paste-like and gelatinous detergent compositions in which the precursor compounds can be incorporated are known from the art and various formulations have been proposed, e.g. in U.S. Pat. Nos. 2,864,770; 2,940,938; 4,772,412; 3,368,977; GB-A-1,205,711; 1,270,040; 1,292,352; 1,370,377; 2,194,536; DE-A-2,233,771; and EP-A-0,028,849.

These are compositions which normally comprise a non-aqueous liquid medium with or without a solid phase dispersed therein. The non-aqueous liquid medium may be a liquid surfactant, preferably a liquid nonionic surfactant; a non-polar liquid medium, e.g. liquid paraffin; a polar solvent, e.g. polyols, such as glycerol, sorbitol, ethylene glycol, optionally combined with low-molecular monohydric alcohols, e.g. ethanol or isopropanol; or mixtures thereof.

The solid phase can be builders, alkalis, abrasives, polymers, clays, other solid ionic surfactants, bleaches, fluorescent agents and other usual solid detergent ingredients.

The following non-limiting Examples will more fully illustrate the embodiments of the invention.

EXAMPLE I

The following Example illustrates the manufacture of various cationic nitrile peroxyacid precursor compounds according to the invention.

BY DIRECT SYNTHESIS

(i) Trimethylammonium acetonitrile p-toluene sulphonate

Dimethylamino acetonitrile (4.2 g, 0.05 mole) was dissolved in dry acetonitrile (50 ml) in a 100 ml RB flask provided with condenser, calcium chloride drying tube, and anti-bumping granules. Methyl p-toluene sulphonate (9.3 g, 0.05 mole) was added and the solution refluxed for 5 hours. The flask was cooled in ice, and the white solid crystalline solid filtered off, washed with ice-cold dry acetonitrile and then vacuum-dried to give 10.65 g of product, yield 78.8%: 'H NMR ($\sigma$, $D_2O$) 2.4 (s, 3H, $CH_3$-Ar), 3.4 (s, 9H, $(CH_3)_3N^+$), 7.4+7.7 (dd, 4H, ArH) ppm.

(ii) 2-Trimethylammonium propionitrile p-toluene sulphonate

This material was prepared, using a method analogous to that in (i) vide supra, except that 2-dimethyl aminopropionitrile was used instead of dimethylamine acetonitrile, and further fractions were obtained by evaporating off the acetonitrile and sonicating with ether. A white solid, 7.99 g yield, was obtained: 'H NMR assay ($D_2O$, trioxan) 98% ($\sigma$, $D_2O$) 1.9 (s, 3H, $CH_3$—C), 2.4 (s,.3H, $CH_3$-Ar), 3.35 (s, 9H $(CH_3)_3N^+$) 7.4-7.7 (2d, 4H, ArH) ppm.

(iii) 2-Trimethylammonium butyronitrile p-toluene sulphonate

This material was prepared, using a method analogous to that in (i) vide supra, except that 2 dimethylamino butyronitrile was used instead of dimethylamino acetonitrile. Three product fractions (18.6 g, yield 100%) were obtained. 'H NMR assay ($D_2O$, trioxan) 97.5% ($\sigma$, $D_2O$) 1.2 (t, 3H, $CH_3$—$CH_2$), 2.1 +2.3 (m, 2H, $CH_2$), 2.4 (s, 3H ($CH_3$—Ar) 3.4 (s, 9H, $(CH_3)_3$-$N^+$), 7.75 (2d, 4H, ArH) ppm.

(iv) 2-Trimethylammonium-2-methyl propionitrile p-toluene sulphonate

This material was prepared, using a method analogous to that in (i) vide supra, except that 2-dimethylamino-2-methyl propionitrile was used instead of dimethylamino acetonitrile. The reaction mixture was cooled in acetone/cardice and a white crystalline solid was filtered off and vacuum-dried (5.3 g). A further fraction was obtained by evaporating off the acetonitrile, and ether-extracting the residual solid (8.3 g, total yield 93%). 'H NMR assay ($D_2O$, trioxan) 73% and 86%, respectively ($\sigma$, $D_2O$) 2.0 (s, 6H, $CH_3$)$_2$—C), 2.4 (s, 3H, $CH_3$—Ar), 3.35 (s, 9H $(CH_3)_3N^+$), 7.4-7.7 (2d, 4H, ArH) ppm.

(v) Phenyl trimethylammonium acetonitrile p-toluene sulphonate

This material was prepared, using a method analogous to that in (i), vide supra, except that phenyl dimethylamino acetonitrile was used instead of dimethylamino acetonitrile. A white solid (11.88 g, yield 68%) was obtained: 'H NMR assay ($D_2O$, trioxan) 102.9% ($\sigma$, $D2O$) 2.4 (s, 3H, $CH_3$—Ar), 3.3 (s, 9H, $CH_{33}N^+$), 7.4 (d, 2H, 7.65-7.85 (m, 7H, ArH) ppm.

(vi) Trimethylammonium acetonitrile p-dodecyl benzene sulphonate

Dimethylamino acetonitrile (2.1 g, 0.025 mole) was dissolved in dry acetonitrile (50 ml) in a 100 ml RB flask provided with condenser, drying tube and anti-bumping granules. Methyl dodecylbenzene sulphonate (8.5 g, 0.025 mole) was added, and the solution refluxed for 8 hours. On cooling to room temperature, white crystals were formed and were filtered off, washed with a little cold acetonitrile and vacuum-dried at room temperature to give 6.3 g product, yield 59%. 'H NMR assay ($D_2O$, trioxan) 93%, (o, D) 0.6-1.6 (complex unresolved, 24H, $C_{12}H_{25}$),

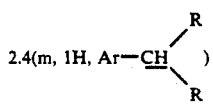

2.4(m, 1H, Ar—CH)

3.25 (s, 9H, $(CH_3)_3N^+$), 7.2-7.8 (m, 4H, ArH) ppm.

(vii) 2 Trimethylammonium propionitrile p-dodecyl sulphonate

This material was prepared, using a method analogous to that in (vi), vide supra, except that 2-dimethylamino propionitrile was used instead of dimethylamine acetonitrile. The product would not crystallize from acetonitrile, and so it was evaporated off and the sticky solid was sonicated with dry ether to remove unreacted starting materials. The solid was vacuum-dried over $P_2O_5$ to give 5.45 product, yield 62%. 'H NMR assay ($D_2O$, trioxan) 91% (o, D20) 0.6-1.6 (complex unresolved, 24H, $C_{12}H_{25}$), 1.7 (s, 3H, $CH_3$—CH), 3.2 (s, 9H, $(CH_3)_3N^+$)

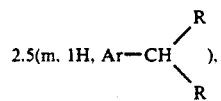

2.5(m, 1H, Ar—CH), 7.2-7.5 (2d, 4H, Arh) ppm.

(viii) Trimethylammonium phenyl acetonitrile p-dodecyl benzene sulphonate

This material was prepared, using a method analogous to that in (vi), vide supra, except that dimethylamino phenyl acetonitrile was used instead of dimethylamino propionitrile. A white solid (7.66 g, yield 76%) was obtained. 'H NMR assay ($CDCl_3$, trioxan) 99% ($\sigma$, $CDCl_3$) 0.7-1.7 (complex unresolved, 24H, $C_{12}H_{25}$),

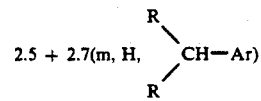

2.5 + 2.7(m, H, CH—Ar)

3.55 (s, 9H, $(CH_3)_3N^+$), 6.85 (s, IH, N—CH), 7.15 (d, 2H, ArH, 7.5 (d, 2H, ArH) 7.6 (d, IH, ArH), 7.8 (2d, 4H, ArH) ppm.

(ix) Trimethylammonium 2-methyl propionitrile p-dodecyl benzene sulphonate

This material was prepared, using a method analogous to that in (vii), vide supra, except that 2-dimethylamino-2-methyl propionitrile was used instead of 2-dimethylamino propionitrile. A white solid, 5.51 g, yield 61%, was obtained. 'H NMR assay (D₂O trioxan) 83.6% ($\sigma$, D₂O) 0.6-1.5 (complex unresolved, 24H, C₁₂H₂₅), 1.8 (s, 6H, (CH₃)₂—C)

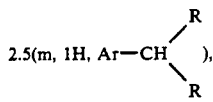

2.5(m, 1H, Ar—CH), 3.2 (s, 9H, (CH₃)₃N⁺), 7.2-7.8 (2d, 4H, ArH) ppm.

BY ION EXCHANGE

(a) Trimethylammonium acetonitrile laurate

Trimethylammonium acetonitrile chloride (1.0 g, 0.007435 mole) was dissolved in methanol (20 ml) in a test tube. Sodium laurate (1.65 g, 0.007435 mole) was dissolved in boiling methanol (50 ml) and the two solutions mixed. The solution was evaporated to dryness and the solid heated with ethanol (60 ml). A granular precipitate of sodium chloride settled out and was filtered off, but less than the theorectical amount was obtained. The ethanolic solution was evaporated to dryness, azeotroped twice with IPA to give a lumpy solid containing white and fawn components (2.08 g, yield 93%). 'H NMR ($\sigma$, D₂O) 0.85 (t, 3H, CH₃⁻) 1.3 (s, 16H, CH₃—(CH₂)₈), 1.55 (m, 2H, CH₂CH₂CO⁻) 3.4 (s, 9H, (CH₃)₃N⁺) ppm. The ratio of quat to laurate was 1.3:1.

(b) 2-Trimethylammonium propionitrile laurate

This material was prepared, using a method analogous to that in (a), vide supra, except that 2-trimethylammonium propionitrile methosulphate was used instead of trimethylammonium acetonitrile. IPA was used instead of ethanol as sodium methosulphate is even less soluble in it, while the quaternary salt is soluble. Less than the theoretical amount of sodium methosulphate was obtained, and more than the theoretical amount of product was obtained (1.53 g). On preparing a sample for NMR analysis in D₂O, a white insoluble solid separated out and the spectrum showed the presence of quat only. This was attributed to lauric acid being formed from the action of bisulphate, the hydrolysis product of methosulphate. When the NMR was repeated in DMSO, the spectra were consistent and the ratio of quat:laurate was 1:1. Similar problems were found with the 2-trimethylammonium butyronitrile laurate preparation.

(c) Trimethylammonium acetonitrile dodecyl sulphate

Trimethylammonium acetonitrile (1.0 g, 0.007435 mole) and sodium dodecyl sulphate (2.14 g, 0.007435 mole) were weighed into a 250 ml rotary evaporator flask. Methanol (100 ml) was added and the mixture heated until a clear solution was obtained. The methanol was evaporated off and IPA (150 ml) was added, and the mixture warmed. A granular precipitate of sodium chloride separated out and was filtered off. The amount obtained was less than the theoretical amount. The IPA-soluble fraction was evaporated to dryness to give 3.4 g of solid and this was further dried under vacuum. 'H NMR ($\sigma$, D₂O) 0.9 (t, 3H, CH₃—C), 1.3 (m, 18H, CH₃(CH₉) 1.7 (m, 2H, CH₂CH₂SO₄⁻), 3.4 (s, 9H, (CH₃)₃N⁺), 4.1 ppm (t, 2H, —CH₂SO₄⁻) ppm. The ratio of quaternary to dodecyl sulphate was 1.03:1.

(d) 2-Trimethylammonium propionitrile dodecyl sulphate

This material was prepared, using a method analogous to that in (c), vide supra, except that 2trimethylammonium propionitrile methosulphate was used instead of trimethylammonium acetonitrile chloride. A clear viscous oil (1.65 g) was obtained (yield 985). 'H NMR ($\sigma$, D2O) 0.85 (t, 3H, CH₃CH₂), 1.3 (m, 18H, CH₃(CH₂)₉⁻), 1.7 (m, 2H, CH₂CH₂SO₄⁻), 1.85 (d, 3H, CH₃—CH), 3.3 (s, 9H, (CH₃(₃N⁺) 4.0 (t, 2H, CH₂SO₄⁻), 5.0 (q, 1H, CH) ppm. The ratio of quaternary to dodecyl sulphate was 1:1.

(e) 2-Trimethylammonium butyronitrile dodecylsulphate

This material was prepared, using a method analogous to that in (c), vide supra, except that trimethylammonium butyronitrile methasulphate was used instead of trimethylammonium acetonitrile chloride. The starting material was not pure and an amount, more than expected, of the known sticky solid was obtained. Methosulphate was still present in the product fraction (28%). 'H NMR ($\sigma$, D2O) 0.85 (t, 3H, CH₃(CH₂)₉⁻), H (t, 3H, CH₃CH₂⁻) 1.3 (m, 18H, CH₃(CH₂)₉⁻, 1.7 (m, 2H, CH₂CH₂SO₄⁻), 2.1-2.3 (2m, CH₃CH₂⁻) 3.35 (s, 9H, (CH₃)₃-N⁺), 3.75 (s, 3h, CH₃SO₃⁻), 4.0 (t, 2H, CH₂SO₄⁻) 4.9 (q, 1H, CH) ppm. The ratio of quaternary to dodecyl sulphate was 1:1.06.

EXAMPLES II and III

These Examples show the influence of counter anions on the equilibrium Relative Humidity of cationic nitriles. The experiments were carried out with samples in closed containers at 28° C., in which the relative humidity can be adjusted and varied.

The equilibrium RH is the relative humidity of the headspace at which the sample commences to take up water and deliquesce.

| Compound | Counter anion | Eq. RH (%) |
| --- | --- | --- |
| A. (CH₃)₃N⁺—CH₂CN | Cl⁻ | <30 |
| B. (CH₃)₃N⁺—CH₂CN | Me—SO₄⁻ | 40 |
| C. C₂H₅(CH₃)₂N⁺—C(CH₃)₂—CN | Eth—SO₄⁻ | 40 |
| II (CH₃)₃N⁺—CH₂—CN | CH₃—C₆H₄—SO₃⁻* | 85 |
| III (CH₃)₃N⁺—CH(CH₃)—CN | C₁₂H₂₅—C₆H₄—SO₃⁻** | 80 |

*p-toluene sulphonate anion
**dodecyl benzene sulphonate anion: compound III started to gel at RH 60% and deliquesce at 80% RH.

EXAMPLE IV

A cationic nitile of formula:

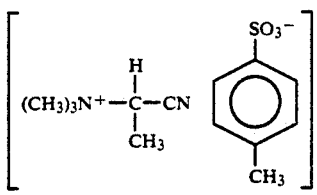

was used in model experiments with sodium perborate at peroxide to nitrile mole ratio of 10:1, in 30 minutes' isothermal washes at 20, 40 and 60° C. at pH 10 using tea-stained test cloths.

The results obtained from repeated tests expressed as $\Delta R_{460}*$ (reflectance) are as follows:

| Temperature | $\Delta R460*$ |
|---|---|
| 20° C. | 21 |
| 40° C. | 24 |
| 60° C. | 21 |

These are similar to the results of control experiments using a cationic nitrile of the art.

Similar bleaching results were observed when the experiments were repeated with the following other tosylate anion cationic nitriles:

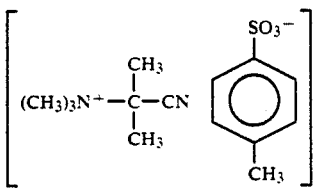

(1)

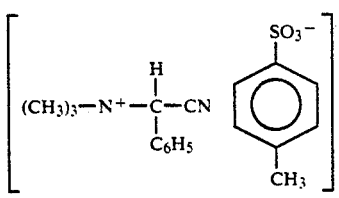

(2)

EXAMPLE V

The following two cationic nitriles (a) and (b) were used in Tergotometer washing experiments with a base powder formulation (A).

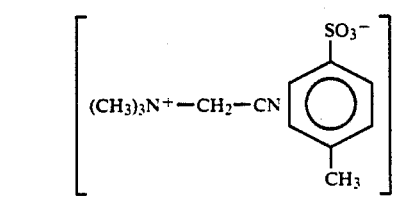

(a) Trimethyl ammonium acetonitrile p-toluene sulphonate

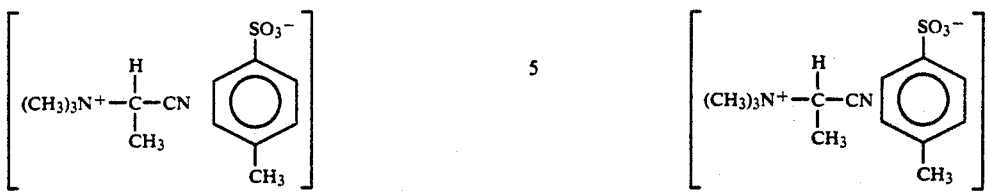

(b) Trimethyl ammonium propionitrile p-toluene sulphonate

| Base powder formulation (A) | % by weight |
|---|---|
| Anionic surfactant | 8 |
| Nonionic surfactant | 13 |
| Zeolite | 35 |
| Polymer (CP5 ex BASF) | 5 |
| Sodium carbonate | 16 |
| Sodium silicate | 1 |
| Water and minors | 22 |

Conditions: Tea-stained test cloths; base powder dosage: 4 g/l; time: 30 minutes; temperature: 40° C. isothermal. =1.2 mmol/l;=0.6 mmol/l; peroxide: precursor ratio 10:1.

| Results | $\Delta R460*$ |
|---|---|
| TAED | 9 |
| Nitrile (a) | 24 |
| Nitrile (b) | 25 |

We claim:

1. A bleaching composition comprising:
   (i) a peroxide bleach compound present in an effective amount for bleaching a substrate; and
   (ii) a cationic nitrile precursor present in an effective amount to activate the peroxide bleach compound, the cationic nitrile having the general formula:

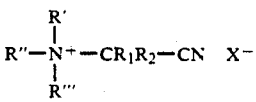

wherein
$R_1$ and $R_2$ are each individually selected from the group consisting of hydrogen and a substituent group containing at least one carbon atom;
R' is a radical selected from the group consisting of straight or branched chain $C_1$-$C_{24}$ alkyl, alkenyl or alkylether radicals and —$CR_1R_2CN$;
R" and R''' are each individually radicals selected from the group consisting of $C_1$-$C_4$ alkyl and hydroxylalkyl radicals;
R" may also be a radical selected from a group having the formula:

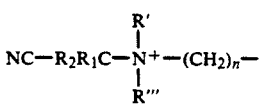

wherein
n is an integer from 1 to about 4; and
$X^-$ is a counter-anion having surfactant activity and containing at least 7 carbon atoms, and wherein X is selected from the group consisting of alkane and paraffin sulphonates; p-toluene sulphonate; dodecyl benzene sulphonate;

$C_{12}-C_{18}$ primary alcohol sulphate; laurylether sulphate; and $C_8-C_{18}$ alkyl carboxylic acid anions.

2. A composition according to claim 1, wherein the substituent $R_1$ and $R_2$ is a radical selected from the group consisting of straight or branched chain $C_1-C_8$ alkyl, alkenyl or alkylether; phenyl; alkylphenyl; and pyridyl radicals.

3. A composition according to claim 1, wherein $R_1$ and $R_2$ radicals are each individually selected from the group consisting of hydrogen, methyl and phenyl.

4. A composition according to claim 1, wherein R' is a radical selected from the group consisting of $C_1-C_4$ alkyl and $-CR_1R_2CN$; R'' and R''' are each $C_1-C_4$ alkyls.

5. A composition according to claim 4, wherein R', R'' and R''' are methyl groups.

6. A composition according to claim 1, wherein the counter-anion is a p-toluene sulphonate ion.

7. A composition according to claim 1, which further comprises, a surface-active material at a level from about 1 to 50% by weight.

8. A composition according to claim 7, comprising:
(a) from 1 to 40% by weight of a surface-active material;
(b) from 5 to 80% by weight of a detergency builder;
(c) from 2 to 40% by weight of a peroxide bleach compound; and
(d) from 0.1 to 20% by weight of a cationic nitrile.

9. A composition according to claim 1, wherein the molar ratio of peroxide to cationic nitrile is from 2:1 to 20:1 and the composition has a 1-5 g/l solution pH of from 8 to 12.

10. A composition according to claim 9, wherein said molar ratio is from 5:1 to 12:1 and said solution pH is from 8.5 to 10.5.

11. A composition according to claim 10, wherein said solution pH is $\geq 9$.

* * * * *